US012636447B2

(12) United States Patent
Meliniotis et al.

(10) Patent No.: US 12,636,447 B2
(45) Date of Patent: May 26, 2026

(54) DRY POWDER INHALER WITH AN ADHERENCE/COMPLIANCE MONITOR

(71) Applicant: VECTURA DELIVERY DEVICES LIMITED, Wiltshire (GB)

(72) Inventors: Andreas Meliniotis, Cambridgeshire (GB); Roger Clarke, Cambridgeshire (GB); Darryl Cotton, Cambridgeshire (GB); John Deamer, Cambridgeshire (GB); Philip Smith, Cambridgeshire (GB); Philip Swanbury, Cambridgeshire (GB); Seth Thomas, Cambridgeshire (GB)

(73) Assignee: VECTURA DELIVERY DEVICES LIMITED (GB)

( * ) Notice: Subject to any disclaimer, the term of this patent is extended or adjusted under 35 U.S.C. 154(b) by 1010 days.

(21) Appl. No.: 17/775,162

(22) PCT Filed: Nov. 17, 2020

(86) PCT No.: PCT/EP2020/082428
§ 371 (c)(1),
(2) Date: May 6, 2022

(87) PCT Pub. No.: WO2021/099328
PCT Pub. Date: May 27, 2021

(65) Prior Publication Data
US 2022/0395652 A1      Dec. 15, 2022

(30) Foreign Application Priority Data

Nov. 18, 2019    (EP) ..................................... 19209856
Nov. 18, 2019    (EP) ..................................... 19209857
Nov. 18, 2019    (EP) ..................................... 19209858

(51) Int. Cl.
*A61M 15/00*          (2006.01)

(52) U.S. Cl.
CPC .... *A61M 15/0065* (2013.01); *A61M 15/0025* (2014.02); *A61M 15/0035* (2014.02);
(Continued)

(58) Field of Classification Search
CPC .......... A61M 15/0025; A61M 15/0026; A61M 15/0028–0063; A61M 15/0065;
(Continued)

(56) References Cited

U.S. PATENT DOCUMENTS

2005/0087473 A1*   4/2005   Fabricius ................ A61J 1/035
                                                        206/534
2006/0191534 A1      8/2006   Hickey et al.
(Continued)

FOREIGN PATENT DOCUMENTS

CN           101176804           5/2008
CN           102458543  A        5/2012
(Continued)

OTHER PUBLICATIONS

Communication of a Notice of Opposition opposing EP4061453B1 dated May 28, 2024 including Opposition filed by PGA Intellectual Property.
(Continued)

*Primary Examiner* — Bradley H Philips
*Assistant Examiner* — Kira B Daher
(74) *Attorney, Agent, or Firm* — Davidson Kappel LLC

(57) ABSTRACT

A dry powder inhaler and an adherence and/or compliance monitor for use with the inhaler are provided. The inhaler has a cover which is pivotable relative to its housing in order to expose a mouthpiece. The monitor has one or more sensors. The inhaler and the monitor have formations for mounting the monitor onto the inhaler. The inhaler and monitor are designed so that when the monitor is mounted (Continued)

onto the housing of the inhaler and the cover is opened, the cover at least partially covers and protects the monitor.

14 Claims, 9 Drawing Sheets

(52) U.S. Cl.
CPC ................. *A61M 2202/064* (2013.01); *A61M 2205/3331* (2013.01)

(58) Field of Classification Search
CPC .......... A61M 15/008; A61M 2202/064; A61M 2205/3331; A61M 2016/0027; A61M 11/003
See application file for complete search history.

(56) References Cited

U.S. PATENT DOCUMENTS

| | | | |
|---|---|---|---|
| 2007/0240712 | A1 | 10/2007 | Fleming et al. |
| 2009/0020113 | A1 | 1/2009 | Watanabe |
| 2010/0031956 | A1 | 2/2010 | Pocock et al. |
| 2010/0192948 | A1 | 8/2010 | Sutherland et al. |
| 2012/0145586 | A1 | 6/2012 | Doyle et al. |
| 2013/0206142 | A1* | 8/2013 | Dudley ............. A61M 15/0026 |
| | | | 128/203.15 |
| 2014/0007875 | A1 | 1/2014 | Aberg et al. |
| 2015/0112707 | A1* | 4/2015 | Manice .................. G16H 40/63 |
| | | | 705/2 |
| 2016/0144141 | A1* | 5/2016 | Biswas ............... A61M 15/009 |
| | | | 128/200.23 |
| 2016/0256639 | A1* | 9/2016 | Van Sickle ............ G16H 20/13 |
| 2017/0325734 | A1* | 11/2017 | Sutherland ........ A61M 15/0041 |
| 2019/0224426 | A1 | 7/2019 | Farina et al. |
| 2019/0298942 | A1 | 10/2019 | Koblenski et al. |
| 2019/0307975 | A1* | 10/2019 | Gupta ............... A61M 15/0048 |
| 2020/0171251 | A1* | 6/2020 | Fato .................. A61M 15/0065 |
| 2021/0085564 | A1* | 3/2021 | Beyleveld ............. A61B 5/742 |
| 2021/0204870 | A1* | 7/2021 | Sutherland ............. G16H 20/40 |

FOREIGN PATENT DOCUMENTS

| | | |
|---|---|---|
| CN | 104080502 A | 10/2014 |
| CN | 105492057 A | 4/2016 |
| CN | 108472461 A | 8/2018 |
| CN | 108939228 | 12/2018 |
| EP | 1 521 609 B1 | 12/2009 |
| EP | 2 666 501 A1 | 11/2013 |
| EP | 3 552 647 A1 | 10/2019 |
| JP | 2000-508943 | 7/2000 |
| JP | 2005-538788 | 12/2005 |
| JP | 2011509727 | 3/2011 |
| RU | 2 163 819 C2 | 3/2001 |
| RU | 2 382 657 C1 | 2/2010 |
| RU | 2 618 931 C2 | 5/2017 |
| RU | 2 691 615 C2 | 6/2019 |
| RU | 2 696 147 C1 | 7/2019 |
| TW | 201620569 A | 6/2016 |
| WO | WO 1994/27555 | 12/1994 |
| WO | WO 1996/13294 | 5/1996 |
| WO | WO1997/040876 | 11/1997 |
| WO | WO 2001/58236 A2 | 8/2001 |
| WO | WO 2001/63368 A2 | 8/2001 |
| WO | WO 2001/68169 A1 | 9/2001 |
| WO | WO 2003/035508 A1 | 5/2003 |
| WO | WO 2003/063754 A1 | 8/2003 |
| WO | WO2003/090811 | 11/2003 |
| WO | WO 2003/095010 A2 | 11/2003 |
| WO | WO 2004/009470 A2 | 1/2004 |
| WO | WO2004/026378 | 4/2004 |
| WO | WO 2005/014089 A1 | 2/2005 |

| | | |
|---|---|---|
| WO | WO 2005/037353 A1 | 4/2005 |
| WO | WO 2007/008858 A2 | 1/2007 |
| WO | WO 2007/012871 A1 | 2/2007 |
| WO | WO 2007/127359 A2 | 11/2007 |
| WO | WO2009/092592 | 7/2009 |
| WO | WO 2009/155581 A1 | 12/2009 |
| WO | WO 2010/036839 A2 | 4/2010 |
| WO | WO2010/135340 A2 | 11/2010 |
| WO | WO 2011/077414 A2 | 6/2011 |
| WO | WO 2011/130583 A2 | 10/2011 |
| WO | WO 2012/026963 A2 | 3/2012 |
| WO | WO 2012/041938 A2 | 4/2012 |
| WO | WO 2012/078804 A1 | 6/2012 |
| WO | WO 2012/085919 A2 | 6/2012 |
| WO | WO 2012/174552 A2 | 12/2012 |
| WO | WO 2013/043063 A1 | 3/2013 |
| WO | WO2013/036881 A2 | 4/2013 |
| WO | WO 2013/175176 A1 | 11/2013 |
| WO | WO 2013/175177 A1 | 11/2013 |
| WO | WO 2014/097294 A1 | 6/2014 |
| WO | WO 2014/147550 A1 | 9/2014 |
| WO | WO 2014/149691 A1 | 9/2014 |
| WO | WO 2014/204511 A2 | 12/2014 |
| WO | WO 2015/030610 A2 | 3/2015 |
| WO | WO 2016/001926 A1 | 1/2016 |
| WO | WO 2016/030521 A1 | 3/2016 |
| WO | WO 2016/033419 A1 | 3/2016 |
| WO | WO2016/043601 | 3/2016 |
| WO | WO2016/033421 A8 | 4/2016 |
| WO | WO2016/081294 A1 | 5/2016 |
| WO | WO 2016/156093 A1 | 10/2016 |
| WO | WO 2016/186859 A1 | 11/2016 |
| WO | WO 2016/187695 A1 | 12/2016 |
| WO | WO 2017/005605 A1 | 1/2017 |
| WO | WO2017/051389 A1 | 4/2017 |
| WO | WO2017/125853 A1 | 7/2017 |
| WO | WO2017/141194 A1 | 8/2017 |
| WO | WO 2018/051346 A1 | 3/2018 |
| WO | WO 2018/104268 A1 | 6/2018 |
| WO | WO 2018/138788 A1 | 8/2018 |
| WO | WO2019/021254 | 1/2019 |
| WO | WO2019/022620 | 1/2019 |

OTHER PUBLICATIONS

Proprietor's Reply to the Grounds of Opposition in EP4061453 filed on Aug. 30, 2024.
Notification of Transmittal of the International Preliminary Report on Patentability from corresponding International Application No. PCT/EP2020/082432, mailed on Feb. 25, 2022.
International Search Report from corresponding International Application No. PCT/EP2020/082432, mailed Jan. 20, 2021.
Written Opinion of the International Searching Authority from corresponding International Application No. PCT/EP2020/082432, mailed on Apr. 13, 2021.
Notification of Transmittal of the International Preliminary Report on Patentability from corresponding International Application No. PCT/EP2020/082422, mailed on Apr. 1, 2021.
International Search Report from corresponding International Application No. PCT/EP2020/082422, mailed Jan. 18, 2021.
Written Opinion of the International Searching Authority from corresponding International Application No. PCT/EP2020/082422, mailed on Jan. 18, 2021.
Notification of Transmittal of the International Preliminary Report on Patentability from corresponding International Application No. PCT/EP2020/082428, mailed on Feb. 24, 2022.
International Search Report from corresponding International Application No. PCT/EP2020/082428, mailed Jan. 14, 2021.
Written Opinion of the International Searching Authority from corresponding International Application No. PCT/EP2020/082428, mailed on Apr. 1, 2021.

* cited by examiner

100

110

140

130

120

100

300

300

320

340

310

330

81

82

DRY POWDER INHALER WITH AN ADHERENCE/COMPLIANCE MONITOR

This application is a U.S. national phase application under 35 U.S.C. of § 371 of International Application No. PCT/ EP2020/082428, filed Nov. 17, 2020, which claims priority of European Patent Application No. EP 19209857.2, filed Nov. 18, 2019, and European Patent Application No. EP 19209856.4, filed Nov. 18, 2019, and European Patent Application No. EP 19209858.0, filed Nov. 18, 2019, the disclosures of which are hereby incorporated by reference herein.

TECHNICAL FIELD OF THE INVENTION

The present invention relates to an inhaler for dry powders containing an active substance for inhalation. In particular, the invention relates to an inhaler and a module for monitoring a patient's adherence and/or compliance.

BACKGROUND TO THE INVENTION

Dry powder inhalers (DPIs) provide an attractive method for administering medicaments, for example to treat local diseases of the airway or to deliver drugs to the bloodstream via the lungs. The medicament is commonly provided as individual doses, such as a strip having a plurality of blisters. The dose is typically dispensed by the user opening a cap or cover to access a mouthpiece, then operating an actuator, such as a button or lever to release the powder and finally inhaling through the mouthpiece. In some inhalers (known as "open-inhale-close" inhalers) the cover itself is the actuator, so that there is no separate actuating lever or button. The inhalers usually have vents to allow air to flow in and a dose counter which displays the number of doses that have been used, or that remain to be used.

The efficacy of treatment is dependent on the patient using the inhaler correctly and as prescribed. Consequently, there is increasing interest in monitoring patient adherence (i.e. whether the patient takes the prescribed number of doses per day, e.g. once or twice daily) and compliance (i.e. whether the patient uses their inhaler correctly, e.g. if they inhale sufficiently strongly to entrain the powder and disperse it into particles that reach the lung).

DPIs typically contain a month's supply of medication. Since adherence/compliance monitors usually contain expensive sensors, electronics etc., they are often provided as separate add-on modules which detachably couple to the inhaler. Thus, when the medication in the inhaler has been used up, the monitor can be detached and then re-attached to a new inhaler.

However, the monitor must not interfere with the operation of the inhaler. For example, to ensure proper actuation of the inhaler and successful dose delivery, the motion of the cover and actuator (if present) must be uninterrupted. Moreover, the air vents and dose counter must be unobstructed. These constraints limit the possible locations for attaching the monitor to the inhaler. Typically therefore, the monitor must fit onto a part that the user holds during operation. For example, WO 2016/111633 and WO 2014/204511 disclose detachable adherence monitors for specific dry powder inhalers. However, the presence of the monitor affects how and where the patient holds the inhaler while operating it, which results in a different user interface compared to the inhaler on its own. This can be confusing for some patients, and could result in patients choosing to remove the monitor.

Moreover, because of these constraints, it may not be straightforward to attach and detach the monitor.

BRIEF DESCRIPTION OF THE INVENTION

The present invention addresses this problem and, in a first aspect, provides a dry powder inhaler having a housing and a cover which is pivotable relative to the housing from a closed position to an open position in order to expose a mouthpiece, wherein the inhaler is designed for use with a monitor having one or more sensors, wherein the housing has one or more formations for attaching the monitor to the inhaler and wherein, when the cover is in the open position, it at least partially covers the formations. Thus, in the open position, the cover at least partially covers the location in which the monitor is mounted. In other words, when the monitor is mounted onto the inhaler and the cover is fully opened, the cover at least partially covers the monitor.

In a second aspect, the invention provides a monitor designed to be used with the inhaler of the first aspect, the monitor having a sensor and formations for attaching the monitor to the inhaler, so that when the monitor is mounted onto the inhaler and the cover is fully opened, the cover at least partially covers the monitor.

The invention has the advantage that the patient does not need to touch the monitor when using the inhaler. In fact, the patient is discouraged or prevented from touching the monitor when the cover is in the open position for inhalation, because the monitor at least partially is situated under the cover. The cover thereby protects the monitor, for example from inadvertent removal and accidental damage. The formations on the housing are preferably accessible when the cover is in the closed position.

The formations on the housing and the monitor perform the function of positioning the monitor on, and attaching the monitor to the inhaler. The formations may be mechanical, for example one or more clip connections, such as pegs or clips on the monitor and corresponding holes or slots on the inhaler, or vice versa. In one embodiment, the housing of the inhaler has one or more clips which are accessible when the cover is in the closed position and at least partially covered by the cover when it is the open position. The formations may facilitate attachment of the monitor to the inhaler by one or more screws. The monitor could also be positioned on and/or attached to the inhaler by magnets.

In a preferred embodiment, the monitor is detachably mountable onto the inhaler.

The sensor may be an optical sensor, for determining the position and/or direction of motion of the cover. The inside of the cover may have markings designed to be read by the monitor in order to determine the position and/or direction of motion of the cover. The sensor may be configured to read the markings so that the monitor can determine the position and/or direction of motion of the cover. Alternatively, the inside of the cover may have one or more cams designed to operate switches on the monitor for determining the position and/or direction of motion of the cover.

In one embodiment, the opening motion of the cover has two stages: in the first stage, moving the cover from the closed position to an intermediate position causes a blister strip to be advanced; and in the second stage, moving the cover from the intermediate position to the open position causes a piercer to pierce an aligned blister.

The monitor may have an inner face that matches the shape of the housing of the inhaler on which it is designed to be mounted and an outer face which corresponds to the curve defined by the rotation of the cover.

The monitor may have a sensor, preferably an optical sensor, for reading a code on the blister strip. The optical sensor may be configured to read the code so that the monitor can determine the position and/or direction of motion of the blister strip.

The monitor may determine the position and/or direction of motion of the blister strip during the first stage of the opening movement of the cover by means of the sensor that reads the code on the blister strip, and determine the position and/or direction of motion of the cover during the second stage by means of the sensor that reads the markings on the inside of the cover. Alternatively, the monitor may have switches on its outer side which are operated by the cams on the inside of the cover of the inhaler, and the monitor may be configured to determine the position and/or direction of motion of the cover in both the first and the second stages of the opening movement of the cover based on the states of the switches.

The monitor may additionally have a pressure sensor for sensing a patient's inhalation on the mouthpiece.

The monitor may have a controller and memory for processing and/or storing information from the sensor(s) and communication means for transmitting information to an external device, such as a computer or smartphone.

In a third aspect, the invention provides a combination of the inhaler of the first aspect and monitor of the second aspect, such as a kit comprising the inhaler and the monitor. Preferably the monitor is mounted onto the inhaler.

BRIEF DESCRIPTION OF THE FIGURES

The invention will now be further described with reference to the Figures, wherein.

DETAILED DESCRIPTION OF THE INVENTION

In the context of dry powder inhalers, the term "adherence" is normally used to refer to whether the patient takes the prescribed number of doses per day, e.g. once or twice daily. The term "compliance" is normally used to refer to whether the patient uses their inhaler correctly, e.g. if they inhale sufficiently strongly to entrain the powder and disperse it into particles that reach the lung. Consequently, a monitor may be designed to measure adherence and/or compliance, according to the type of sensors that it uses, and how they are configured. In the present application, the term "monitor" therefore refers to a module having one or more sensors that is designed to measure and capture information relating to adherence and/or compliance. However, the monitor does not perform any of the functions associated with dosing the medication, such as a piercing or opening blisters/capsules, de-agglomerating the powder or providing a breath-actuation mechanism. The inhaler therefore operates to dispense powder whether the monitor is present or not.

Figure 1A:
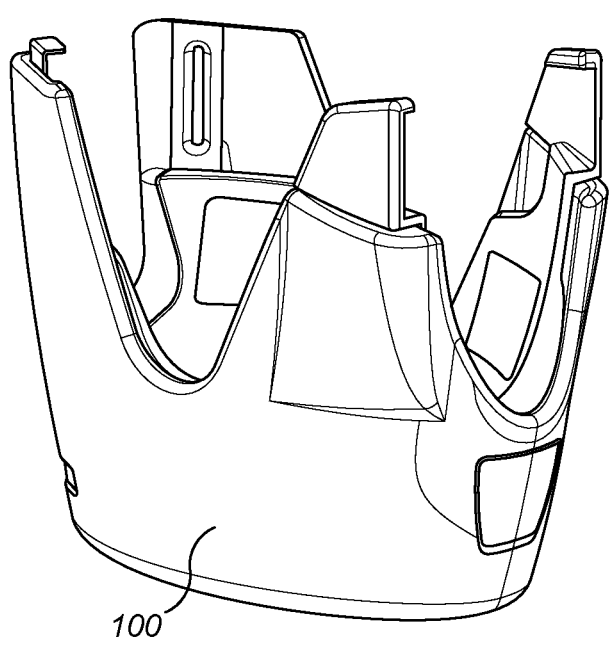
FIG. 1A shows a prior art adherence monitor for the Handihaler® inhaler.
Figure 1B:
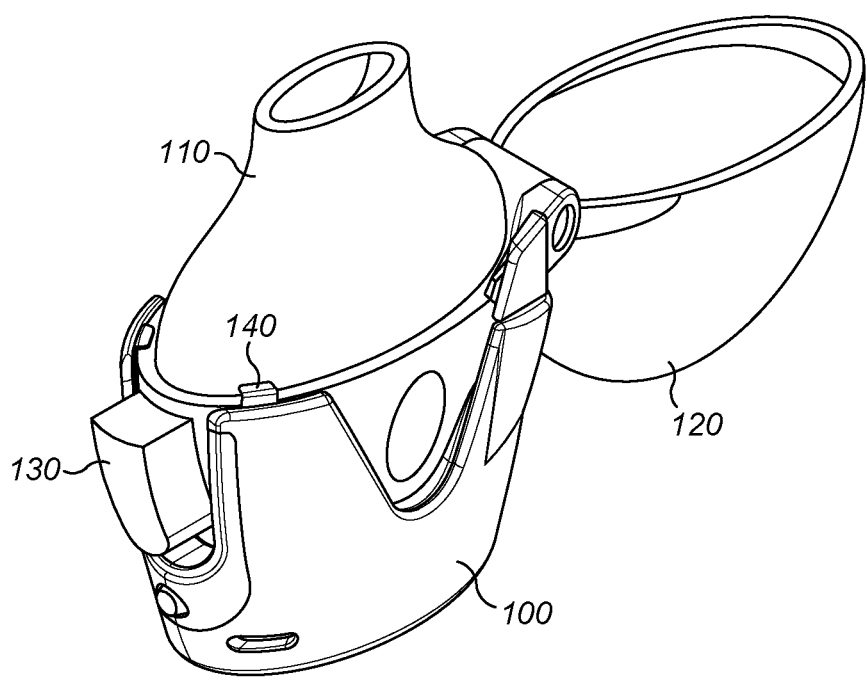
FIG. 1B shows the monitor of FIG. 1A in place on the Handihaler®.
Figure 2A:
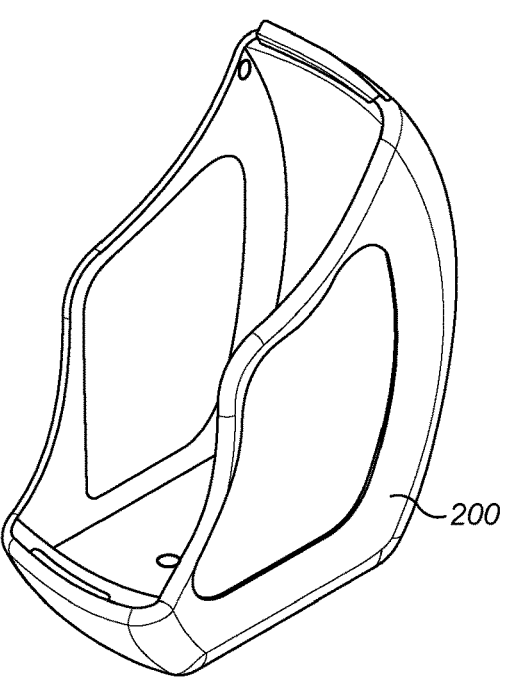
FIG. 2A shows a prior art adherence monitor for the Ellipta® inhaler.
Figure 2B:
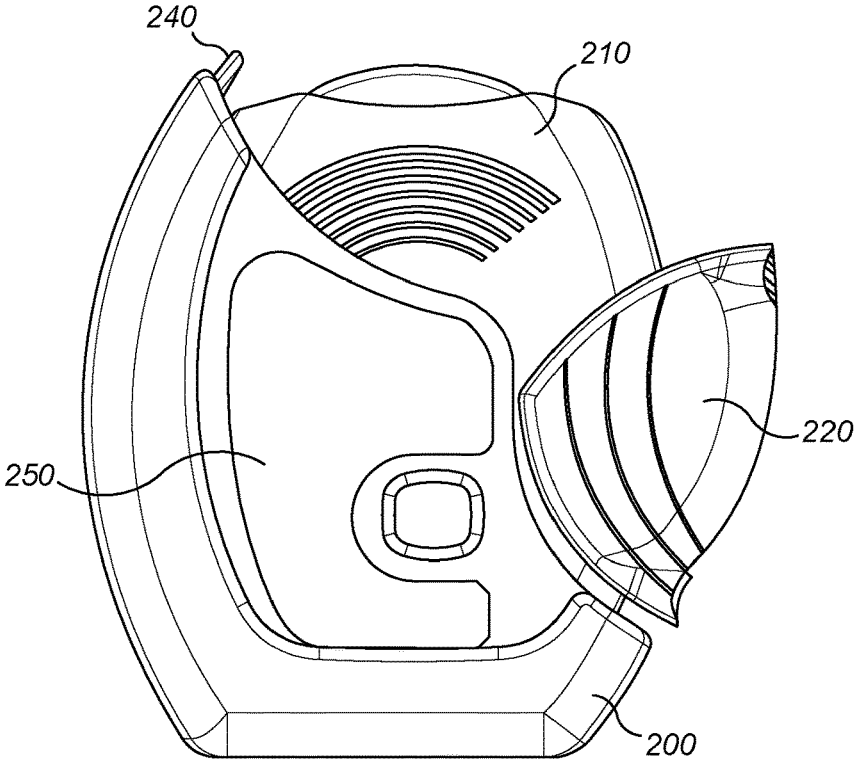
FIG. 2B shows the monitor of FIG. 2A in place on the Ellipta®.
Figure 3A:
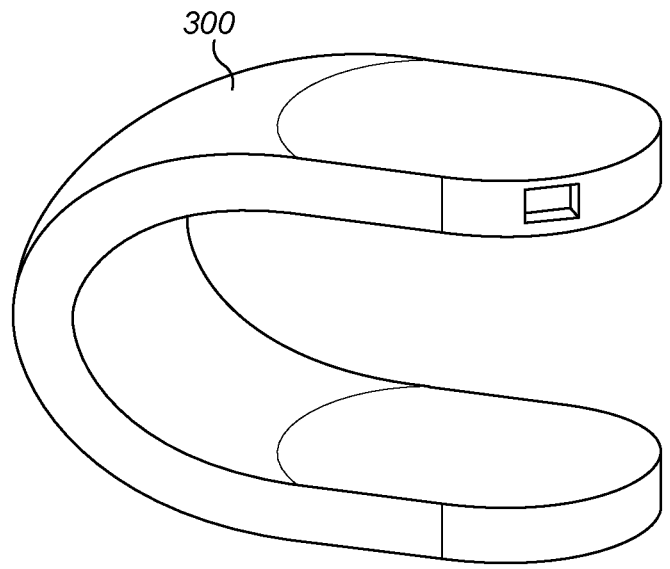
FIG. 3A shows a prior art adherence monitor for the Diskus® inhaler.
Figure 3B:
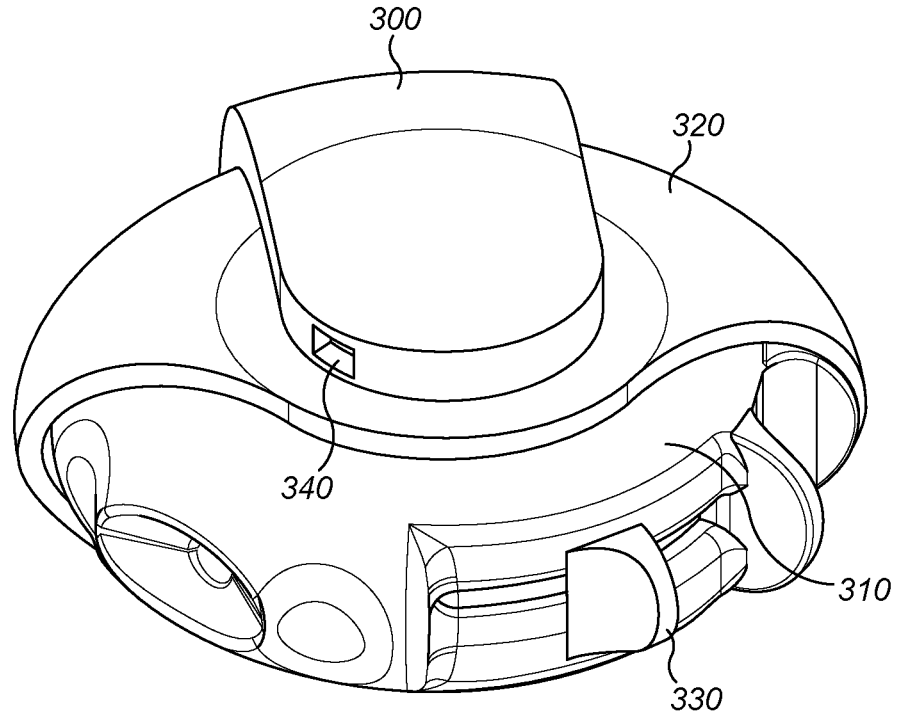
FIG. 3B shows the monitor of FIG. 3A in place on the Diskus®.

WO 2016/111633 discloses detachable adherence monitors which have been retrospectively designed for specific dry powder inhalers, namely the Handihaler® and the Ellipta®, shown in FIGS. 1 and 2 respectively. WO 2014/204511 discloses adherence monitors for the Diskus® dry powder inhaler, shown in FIG. 3. FIGS. 1A, 2A, 3A show the monitors 100, 200, 300 alone; FIGS. 1B, 2B, 3B show them attached to the inhaler 110, 210, 310 in each case.

To attach the monitor 100 to the Handihaler® 110, the user has to slide the inhaler into the monitor at an angle, with the actuator button 130 first, so that the top edge of the inhaler fits under a retaining catch. Then outward pressure is applied to the monitor so that further retaining catches flex and allow the inhaler to fit into the monitor. The cover and mouthpiece may then be pivoted open to insert a capsule containing the powder. Then the actuator button 130 is pressed to pierce the capsule. The monitor has a switch 140 which is activated when the cover is opened/closed and a timer which records the time between opening and closing of the cap. If this time is in a defined range (such as between 3 and 10 seconds), then inhalation is deemed to have taken place.

The monitor 200 is attached to the Ellipta® inhaler 210 by an interference fit. The monitor has a switch 240 which is activated when the cover is opened/closed and a timer which records the time between opening and closing of the cap. It also has transparent sections 250 so that the label on the inhaler is not hidden. To operate the inhaler, the cover 220 is pivoted, which exposes the mouthpiece and also actuates the blister indexing and opening mechanism. The monitor may also have an acoustic sensor for detecting actuation or inhalation.

The monitor 300 for the Diskus® inhaler 310, may be configured as a clip that fits over the top and bottom portions of the inhaler. To operate the inhaler, the cover 320 is opened, then the actuator lever 330 is pressed. The monitor has motion sensors which determine whether or not the motion is characteristic of typical inhaler use. The monitor also has a temperature sensor 340 which can detect the presence of the patient's mouth at the mouthpiece.

In each case, since the monitors must not interfere with the cover or the actuator button/lever, they are designed to fit onto the other part of the inhalers, i.e. the part that the user holds during operation. Consequently, the patient must hold the monitor while operating the inhaler, resulting in a different user experience compared to the inhaler on its own. Moreover, the fact that the patent holds the monitor during inhalation can lead to inadvertent removal of the monitor or accidental damage to it.

An inhaler and monitor of the invention are shown in FIG. 4. FIG. 4A shows the inhaler with a monitor attached, and with the mouthpiece cover in the closed position. FIG. 4B shows the inhaler with the mouthpiece cover in the open position so that the mouthpiece is visible and so that the monitor is covered. FIG. 4C shows the inhaler with the monitor removed and with the mouthpiece cover in the open position. FIGS. 4D and 4E show the monitor detached from the inhaler.

The inhaler shown in FIG. 4 is an "open-inhale-close" inhaler of the type described in WO13/175177, which has a gear mechanism that selectively couples the mouthpiece cover to a blister strip indexing mechanism and also to a piercer. Moving the cover from the closed position to an intermediate position (the first stage of opening) causes the indexing mechanism to advance the blister strip. Then, once an unused blister is in position beneath the piercer, the indexing mechanism is disengaged. Moving the mouthpiece cover from the intermediate position to the fully open position (the second stage) causes the piercer to pierce the aligned blister. The user then inhales through the mouthpiece, which aerosolizes the powder in the pierced blister. However, the invention is not limited to this type of inhaler, and for example, could equally be used with an inhaler which has a passive mouthpiece cover, and a separate actuating lever, as described for example in WO13/175176, or with an inhaler which has a blister disk instead of a blister strip.

The inhaler of the invention preferably has a strip of blisters containing powdered medicament, and a mechanism for advancing the blister strip and for opening the blisters which is operated by an actuator. The opening mechanism is suitably a piercer which is mounted on the underside of the mouthpiece. The actuator drives the indexing mechanism to move a blister into alignment with the piercer and then moves the mouthpiece relative to the housing so that the piercer pierces the aligned blister. The actuator may be a lever which causes indexing of the blister strip and piercing of the blisters. Preferably however, the actuator is formed as part of, or is connected to, the cover, so that rotation of the cover causes indexing of the blister strip and piercing of the blisters. The inhaler may be configured to index and pierce one blister on each actuation. Alternatively, it may index and pierce two (or more) blisters on each actuation. For example, it may deliver two (or more) different formulations or medicaments simultaneously.

The inhaler 1 shown in FIG. 4 is constructed from two shell parts 2, 3 which are joined together to form a housing that contains a blister strip. A detachable monitor 40 is attached to one side of the inhaler. A mouthpiece cover 4 is mounted onto the housing. The cover 4 can be rotated through approximately 100° from the closed position (FIG. 4A) in which it covers and protects a mouthpiece, to a fully open position (FIG. 4B), in which the mouthpiece 5 is exposed so that the user can inhale a dose of medicament.

Once the monitor has been attached to the inhaler, the user does not need to touch it. When the cover is in the closed position, the monitor is located on a part of the inhaler which the patient does not hold when opening the cover (if the inhaler was held in this area, the patient's fingers would obstruct the opening movement of the cover). Consequently, the user interface is exactly the same as when the monitor is not present. Moreover, when the cover is in the open position for inhalation, the monitor is situated under the cover, so that it is protected from accidental damage or inadvertent removal.

The inner face of the monitor matches the shape of the housing of the inhaler on which it is mounted. The outer face is designed to correspond to the curve defined by the rotation of cover. In other words, it is shaped as an arc of a circle centred on the axis of rotation of the cover, with a radius which is slightly less than the radius of the internal surface of the cover. Thus, when the cover is opened there is a small clearance gap (about 0.5-1 mm) between the internal surface of the cover and outer face of the monitor. This maximises the volume of the monitor within the constraint that it must fit under the cover. By appearing as a continuation of the curve of the cover, the outer face also provides a visual cue to aid the user in mounting the monitor in the correct position.

Figure 4A:
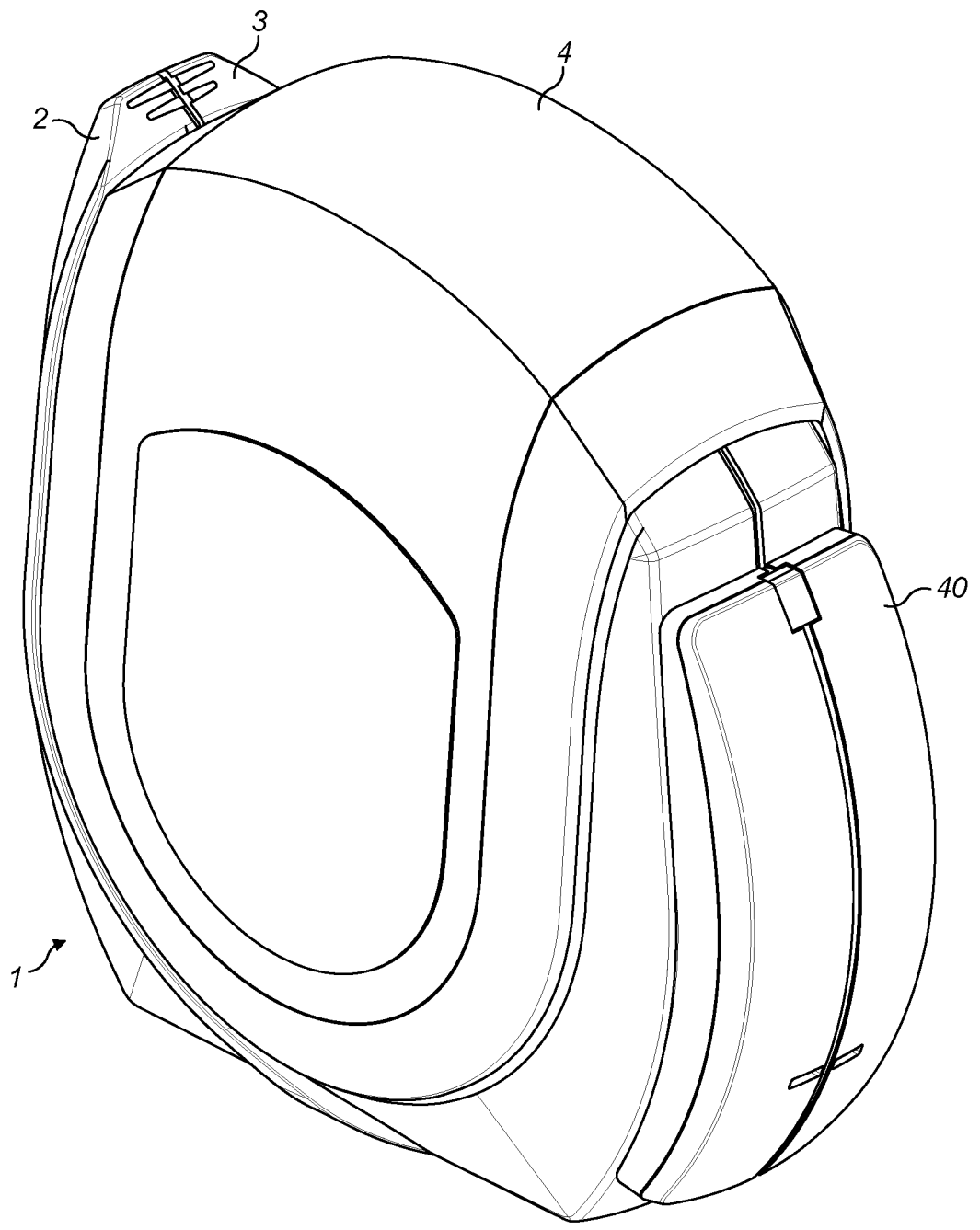
FIG. 4A shows an inhaler and a monitor according to the invention, with the cover in the closed position, so that the mouthpiece is covered.
Figure 4B:
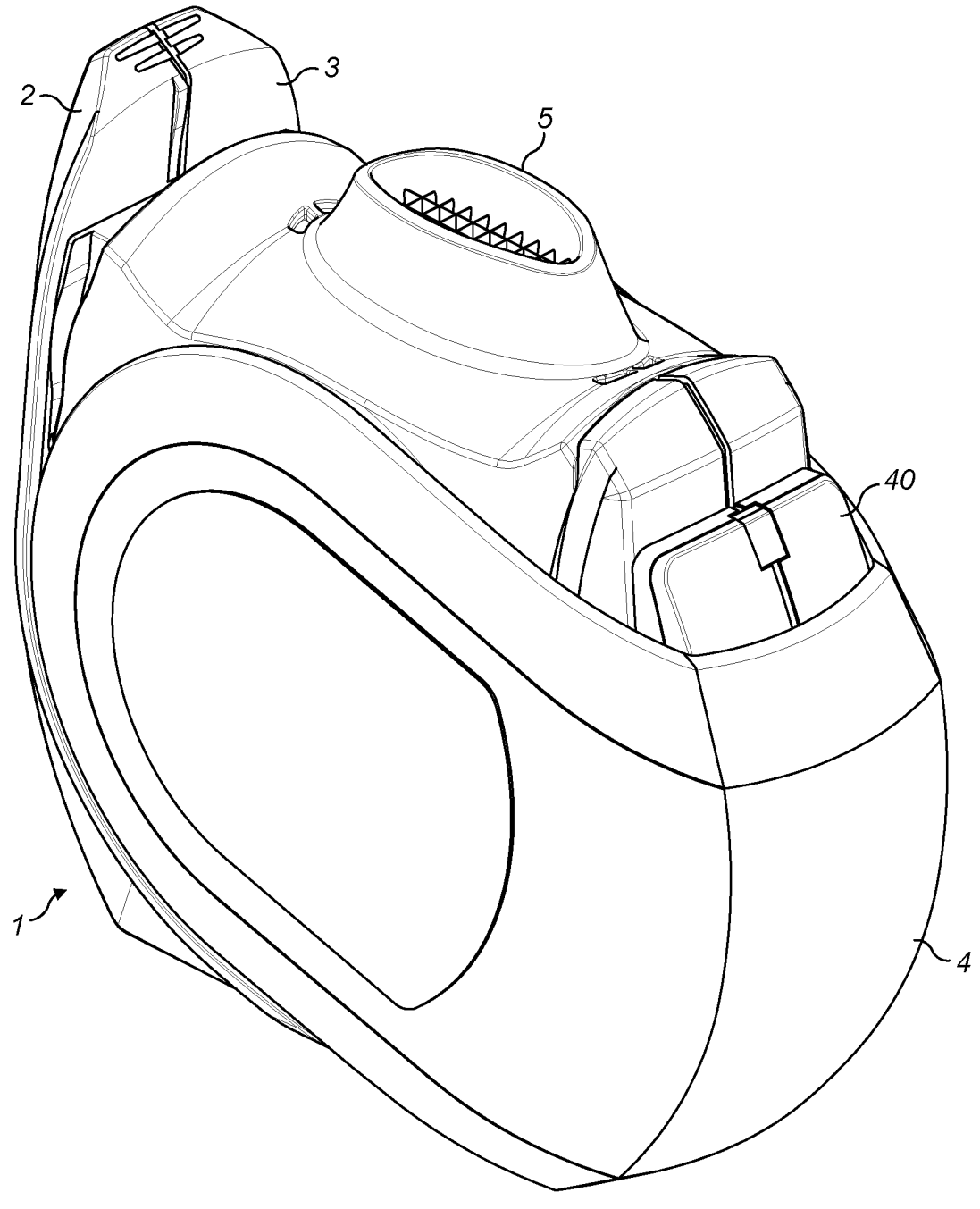
FIG. 4B shows the inhaler of FIG. 4A with the cover in the open position so that the mouthpiece is exposed and the monitor is covered.
Figure 4C:
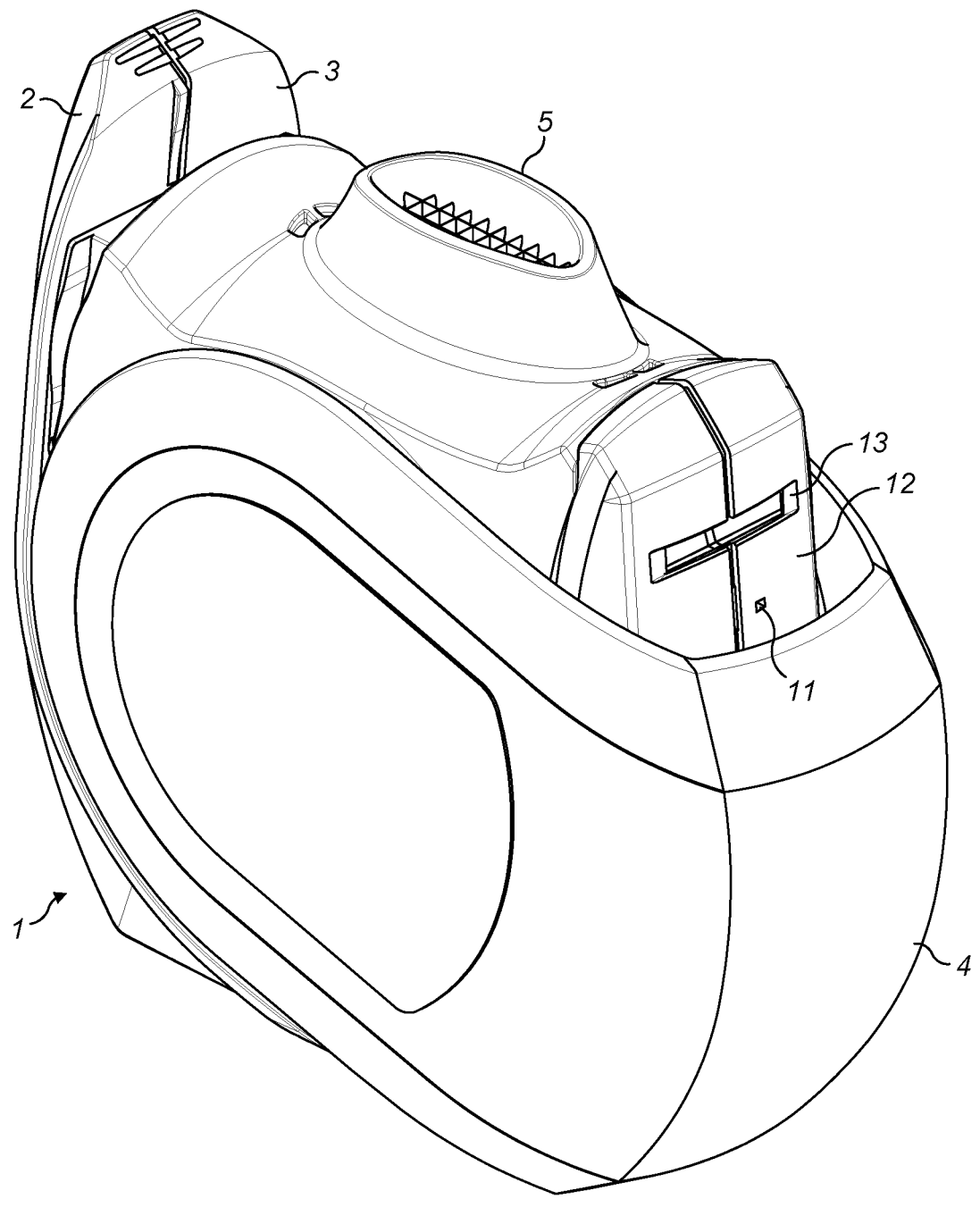
FIG. 4C shows the inhaler of FIG. 4A with the monitor removed and the cover open.

FIG. 4C shows the inhaler with the monitor having been removed. An orifice 11 is visible in the wall 12 of the housing where the monitor was attached; its purpose is described below. A slot 13 for mounting the monitor is also visible. There is a second slot located towards the bottom of the wall 12, but this is not visible in FIG. 4C because it is hidden by the cover 4.

Figure 4D:
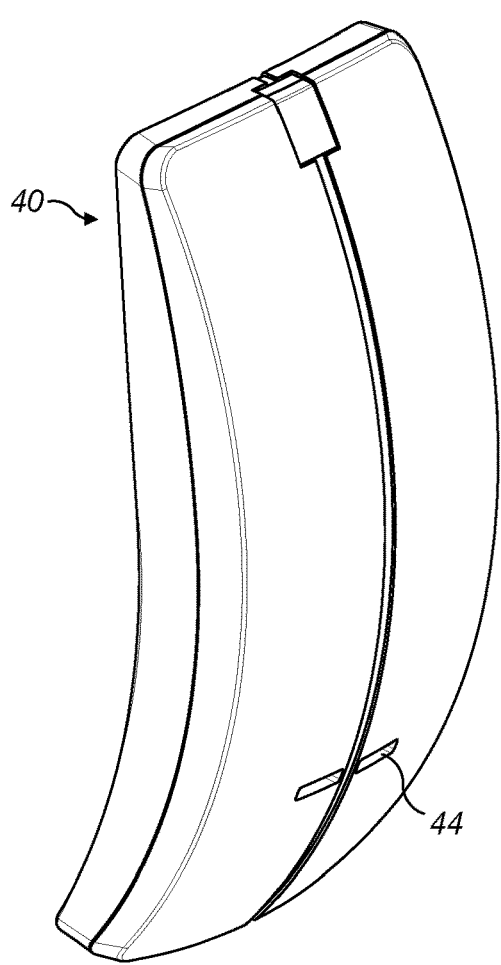
FIGS. 4D and 4E show the monitor removed from the inhaler.

The monitor has an external optical sensor 44 located in a recess on its outer side, shown in FIG. 4D. This sensor is used to determine whether the mouthpiece cover has been fully opened. The cover has markings (e.g. moulded or embossed) on its internal surface which are read by the external optical sensor during the second stage of opening. Hence the monitor can determine whether the cover has been fully opened so that the blister was pierced, or whether actuation was aborted before piercing. This provides a further advantage for "open-inhale-close" inhalers: having the monitor located underneath the cover (when it is in the open position) provides a simple way of determining whether the patient has actually actuated the inhaler, or whether they have only partly opened the cover, and then closed it again. Two such sensors may be used, in combination with a two-part code on the inside of the cover. This allows the monitor to distinguish between four states, so that the direction of motion of the cover can be determined, as well as its position.

Figure 4E:
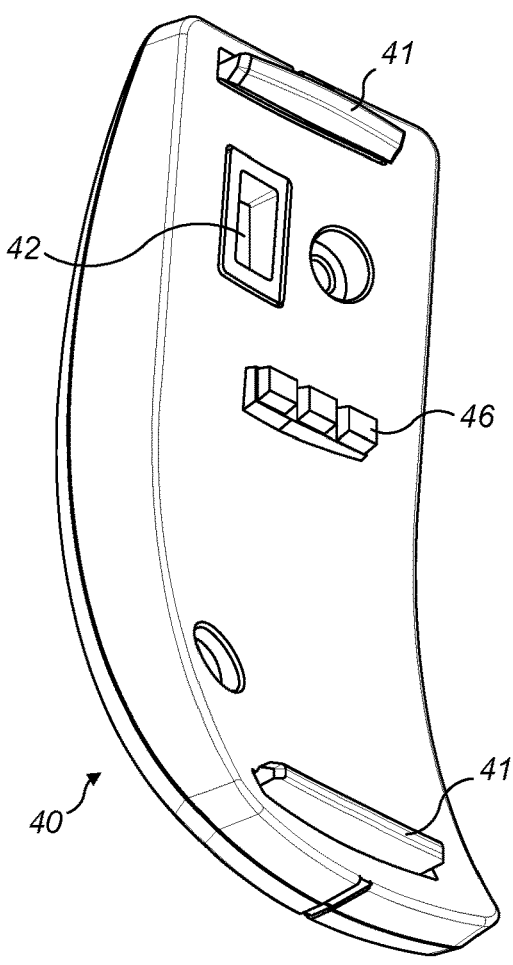

The inside face of the monitor (i.e. the side which abuts the inhaler when the monitor is attached) is shown in FIG. 4E. The monitor 40 has two clips 41 which fit into the corresponding slots 13 in the housing (only one of which is visible in FIG. 4C), and thereby hold the monitor in place when attached to the inhaler. The monitor has a pressure sensor 42, which is located in a recess on the inside face. The pressure sensor abuts the orifice 11, which leads via a channel in the housing to the mouthpiece. The monitor can thereby measure the pressure in the mouthpiece to detect the user's inhalation. The monitor also has three internal optical sensors 46 (for example photomicrosensors). These read a code on the blister strip (for example, a printed bar code), so that the number of doses that have been dispensed or that remain to be dispensed can be determined.

The monitor may be supplied separately from the inhaler, so that one monitor may be used with many different inhalers. The clips and slots allow the monitor to be detachably mounted on the inhaler by an interference fit. Alternatively, the monitor may be fixedly attached to the inhaler, in which case the clips can be welded onto the slots, e.g. by ultrasonic welding.

The position of the cover during the first stage of opening may be monitored by means of the optical sensors 46 on the inner side of the monitor which detect the motion of the code on the blister strip. Monitoring is handed over to the external optical sensor for the second stage in which the blister strip does not move. The external optical sensor is switched on shortly before the indexing mechanism is disengaged, at which point the cover has pivoted far enough to cover the outer optical sensor. This saves battery power because the external optical sensor is only switched on when needed. It also prevents false readings, which could otherwise occur e.g. if the user puts their fingers over the outer sensor.

Figure 5A:
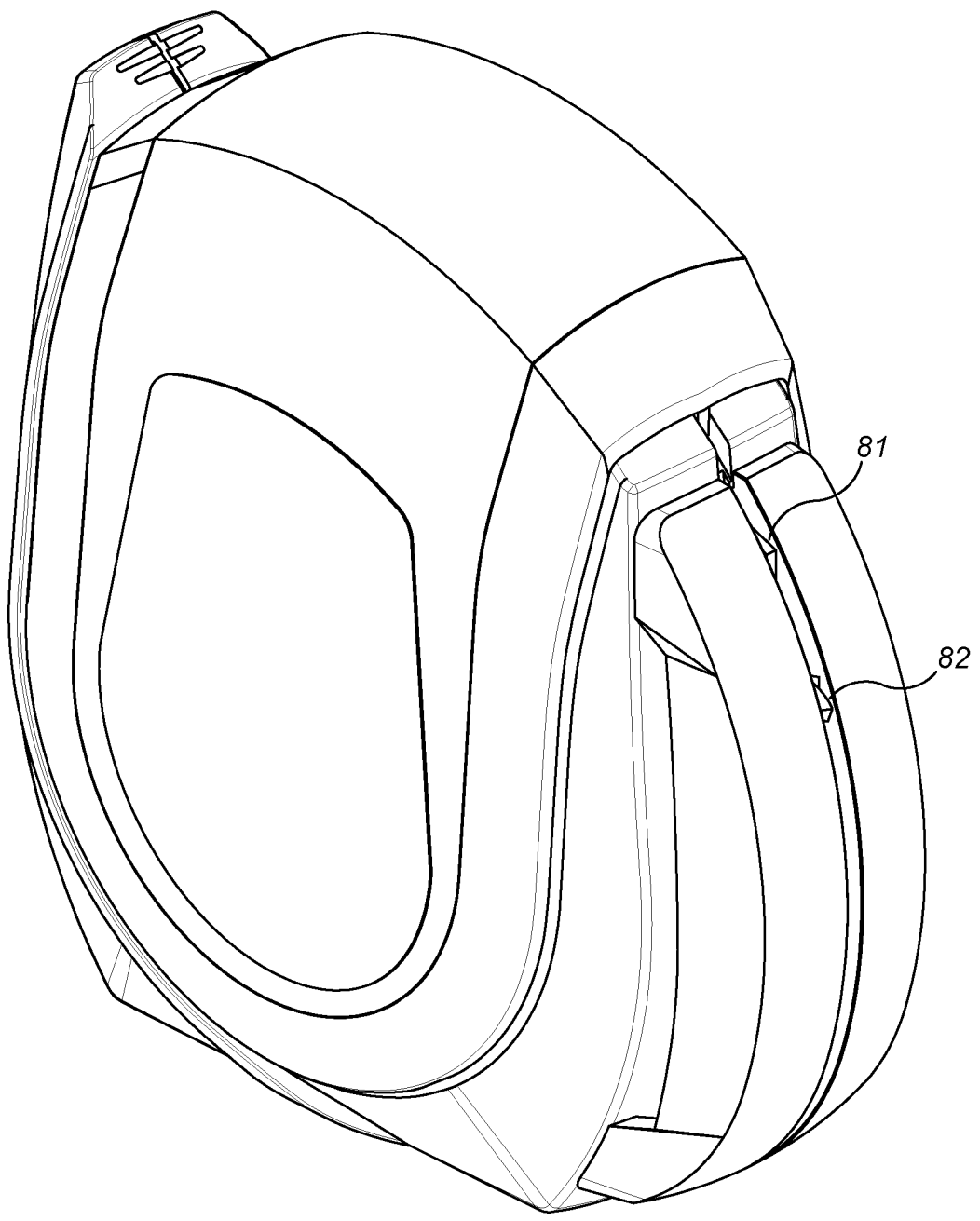
FIG. 5A shows a second embodiment of the monitor that has switches on its outer side.
Figure 5B:
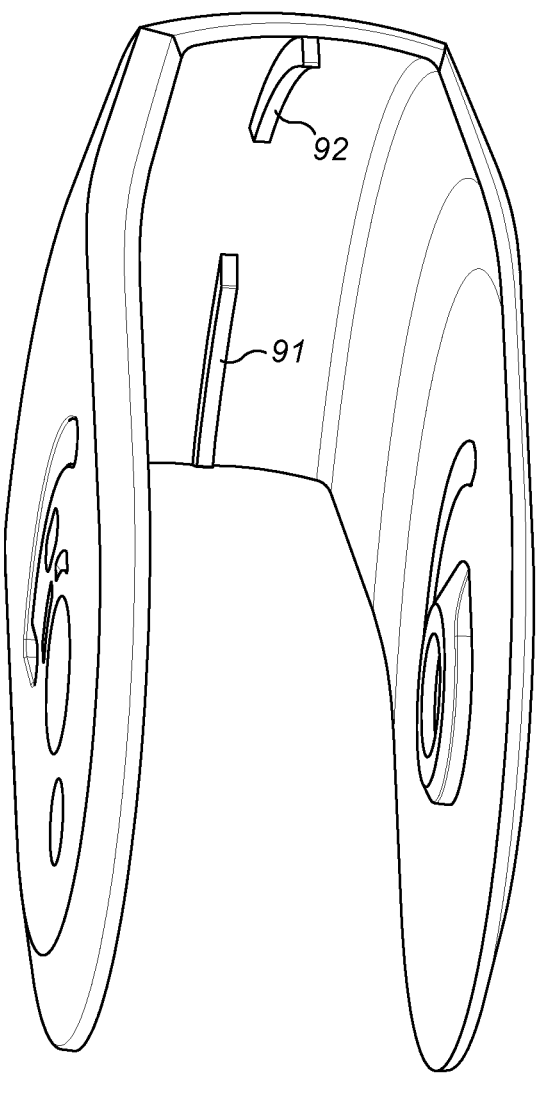
FIG. 5B shows a second embodiment of the mouthpiece cover that has cams on its inside that actuate the switches.

In another embodiment, shown in FIGS. 5A and 5B, the monitor does not have an external optical sensor, but instead has two switches 81, 82. The inside of the cover has two corresponding cams 91, 92 which come into or out of contact with the switches as the cover is opened causing the switches to change state. Each cam causes two changes of state in each switch, so there are eight changes of switch state as the cover is fully opened. This provides two complete cycles of quadrature logic, which allow the monitor to determine the direction of motion of the cover (opening or closing). The switches and cams are arranged so that each change of switch state occurs at a different opening angle spanning both the first and second stages of the opening/closing motion. The monitor counts the changes in switch state and determines the position of the cover from the known angles at which the changes occur. Consequently, there is no need to use the motion of the blister strip to determine the position of the cover during the first stage of opening. Nonetheless, the monitor may have internal optical sensors for reading a code on the blister strip so that the monitor can determine the dose number. The cams and switches allow the monitor to determine whether the cover has been fully opened so that the blister was pierced, or whether actuation was aborted before piercing. The monitor may also have a pressure sensor for detecting inhalation.

This embodiment has the advantage that, due to the close fit between the inside of the cover and the outside of the monitor at all opening angles, the arrangement of cams and switches is simple to implement. Moreover, the power consumption of the monitor is reduced for two reasons. Firstly, there is no need for an external optical sensor. Secondly, the monitor can be switched on, or woken up from a sleep state, whenever one of the switches changes state. This avoids the need for the monitor to be permanently switched on.

The monitor may have a controller and memory (e.g. a suitable microprocessor) which are configured to process and/or store information read from the sensors relating to patient's usage of the inhaler. The monitor may also include communication means to transmit adherence/compliance information (e.g. via bluetooth) to an external device, such as a computer or smartphone. The information may then be displayed to the patient and/or a medical professional, by means of suitable software, for example a smartphone app. The information may additionally or alternatively be stored on the monitor for subsequent interrogation, or wirelessly transmitted to, for example, an online health platform.

The medicament is suitable for administration by inhalation, for example for the treatment of a respiratory disease. It may include one of more of the following classes of pharmaceutically active material: anticholinergics, adenosine A2A receptor agonists, β2-agonists, calcium blockers, IL-13 inhibitors, phosphodiesterase-4-inhibitors, kinase inhibitors, steroids, CXCR2, proteins, peptides, immunoglobulins such as Anti-IG-E, nucleic acids in particular DNA and RNA, monoclonal antibodies, small molecule inhibitors and leukotriene B4 antagonists. The medicament may include excipients, such as fine excipients and/or carrier particles (for example lactose), and/or additives (such as magnesium stearate, phospholipid or leucine).

Suitable β2-agonists include albuterol (salbutamol), preferably albuterol sulfate; carmoterol, preferably carmoterol hydrochloride; fenoterol; formoterol; milveterol, preferably milveterol hydrochloride; metaproterenol, preferably metaproterenol sulfate; olodaterol; procaterol; salmeterol, preferably salmeterol xinafoate; carmoterol; terbutaline, preferably terbutaline sulphate; vilanterol, preferably vilanterol trifenatate or indacaterol, preferably indacaterol maleate.

Suitable steroids include budesonide; beclamethasone, preferably beclomethasone dipropionate; ciclesonide; fluticasone, preferably fluticasone furoate; mometasone, preferably mometasone furoate. In one aspect, the method comprises jet milling mometasone, preferably mometasone furoate in the presence of a liquid aerosol.

Suitable anticholinergics include: aclidinium, preferably aclidinium bromide; glycopyrronium, preferably glycopyrronium bromide; ipratropium, preferably ipratropium bromide; oxitropium, preferably oxitropium bromide; tiotropium, preferably tiotropium bromide; umeclidinium, preferably umeclidinium bromide; Darotropium bromide; or tarafenacin.

The active material may include double or triple combinations such as salmeterol xinafoate and fluticasone propionate; budesonide and formoterol fumarate dihydrate glycopyrrolate and indacaterol maleate; glycopyrrolate, indacaterol maleate and mometasone furoate; fluticasone furoate and vilanterol; vilanterol and umclidinium bromide; fluticasone furoate, vilanterol and umclidinium bromide.

The invention claimed is:

1. A dry powder inhaler having a housing and a cover which is pivotable relative to the housing from a closed position to an open position in order to expose a mouthpiece, wherein the inhaler is designed for use with a monitor having one or more sensors but operates to dispense powder whether the monitor is present or not, wherein the housing has a mechanical or magnetic housing connector used to position and attach the monitor to the inhaler, and wherein when the cover is in the open position, the cover at least partially covers the mechanical or magnetic housing connector wherein an inside of the cover has one or more cams designed to operate switches on the monitor for determining a position and/or direction of motion of the cover.

2. The dry powder inhaler according to claim 1, wherein the mechanical or magnetic housing connector is accessible when the cover is in the closed position.

3. The dry powder inhaler according to claim 1, wherein the mechanical or magnetic housing connector is a clip connections.

4. The dry powder inhaler according to claim 1, wherein the mechanical or magnetic housing connector is adapted for detachably mounting the monitor onto the inhaler.

5. The dry powder inhaler according to claim 1, wherein:
in a first stage, moving the cover from the closed position to an intermediate position causes a blister strip to be advanced;
in a second stage, moving the cover from the intermediate position to the open position causes a piercer to pierce an aligned blister.

6. A dry powder inhaler according to claim 1 which has the monitor having the one or more sensors and further has a mechanical or magnetic monitor connector to position and attach the monitor to the inhaler, so that when the monitor is mounted onto the inhaler and the cover is in the open position, the cover at least partially covers the monitor.

7. The dry powder inhaler according to claim 1, wherein the monitor is mounted onto the inhaler, the monitor having one or more sensors and having a mechanical or magnetic monitor connector to position and attach the monitor to the inhaler, wherein when the cover is in the open position, the cover at least partially covers the monitor.

8. The dry powder inhaler according to claim 7, wherein the mechanical or magnetic monitor connector is a clip connections that connects with a corresponding clip connections on the inhaler.

9. The dry powder inhaler according to claim 7, wherein the monitor is detachably mounted onto the inhaler.

10. The dry powder inhaler according to claim 7, wherein the monitor has an inner face that matches the shape of the housing of the inhaler on which it is mounted and an outer face which corresponds to the curve defined by the rotation of the cover.

11. The dry powder inhaler according to claim 7, wherein the sensor is an optical sensor for reading a code on the blister strip and wherein in a first stage, moving the cover from the closed position to an intermediate position causes a blister strip to be advanced;

in a second stage, moving the cover from the intermediate position to the open position causes a piercer to pierce an aligned blister.

12. The dry powder inhaler according to claim 7, wherein the monitor has switches on its outer side which are operated by the one or more cams and further wherein the monitor is configured to determine the position and/or direction of motion of the cover based on the states of the switches.

13. The dry powder inhaler according to claim 7, wherein the one or more sensors comprises a pressure sensor for sensing a patient's inhalation on the mouthpiece.

14. The dry powder inhaler according to claim 7, wherein the monitor further comprises a controller and memory for processing and-/-or storing information from the sensor(s) and communication means for transmitting information to an external device.

\* \* \* \* \*